United States Patent [19]
DeLaTorre

[11] Patent Number: 6,041,786
[45] Date of Patent: Mar. 28, 2000

[54] APPARATUS FOR MAINTAINING A GAP BETWEEN CLOTHING AND THE WOUND OF A PATIENT

[76] Inventor: Manuel DeLaTorre, 2369 W. Hardies Rd., Gibsonia, Pa. 15044

[21] Appl. No.: 09/128,198

[22] Filed: Aug. 3, 1998

[51] Int. Cl.[7] .................................................... A61F 13/00
[52] U.S. Cl. ............................................ 128/888; 128/889
[58] Field of Search ................................. 128/846, 887, 128/888, 889, 891, 892; 2/22–24

[56] References Cited

U.S. PATENT DOCUMENTS

| | | |
|---|---|---|
| 706,250 | 8/1902 | Müller . |
| 2,520,436 | 8/1950 | Russell .................................... 128/888 |
| 2,663,020 | 12/1953 | Cushman ........................................ 2/2 |
| 3,026,824 | 3/1962 | Stevens .................................... 128/888 |
| 3,176,686 | 4/1965 | Barnes .................................... 128/132 |
| 3,556,096 | 1/1971 | Fuller et al. ............................. 128/171 |
| 4,000,737 | 1/1977 | Horn ......................................... 128/154 |
| 4,159,021 | 6/1979 | Casburn .................................. 128/149 |
| 4,450,845 | 5/1984 | Engle ...................................... 128/743 |
| 4,641,641 | 2/1987 | Strock ..................................... 128/888 |
| 4,905,681 | 3/1990 | Glascock ................................. 128/155 |
| 5,062,433 | 11/1991 | Kummer ................................. 128/888 |
| 5,524,641 | 6/1996 | Battaglia ................................. 128/846 |
| 5,557,804 | 9/1996 | Ovortrup ................................ 128/888 |
| 5,615,691 | 4/1997 | Huffman ................................. 128/891 |

*Primary Examiner*—Michael A. Brown
*Attorney, Agent, or Firm*—Webb Ziesenheim Logsdon Orkin & Hanson, P.C.

[57] ABSTRACT

An apparatus used with clothing for maintaining a gap between the clothing and a wound of a patient using at least one spacer attached to the clothing and contacting an area of the patient's skin adjacent the wound to provide a gap between the clothing material and the wound.

20 Claims, 3 Drawing Sheets

6,041,786

APPARATUS FOR MAINTAINING A GAP BETWEEN CLOTHING AND THE WOUND OF A PATIENT

BACKGROUND OF THE INVENTION

1. Field of the Invention

The invention relates to protectors for a wound such as a surgical chest incision and particularly relates to the use of spacers to eliminate contact between any part of the wound and clothing that may be worn over the wound.

2. Background of the Invention

Major surgical procedures on the chest and upper abdomen usually result in a long incision that remains sensitive for weeks after it is surgically closed. During this time the slightest touching on the wound by clothing may cause severe irritation until healing produces scar tissue that is tough and elastic.

The problem is aggravated by the absence of bandages over the incision. Current medical practice for many incisions requires that the wound be open to air and free from any bandage to reduce the danger of infection. Therefore, the incision is exposed to clothing from the very first hours after any operation producing the wound.

U.S. Pat. No. 4,000,737 to Horne discloses a frame-like structure which may be positioned over an incision so material such as clothing may not contact the incision. This device, using an adhesive bond, is adapted to adhere to the skin surface around the incision. As a result, application of the device to an individual may become cumbersome and removal may be difficult and painful. Furthermore, the device is limited to application on parts of the body that do not experience significant stretching or compression, such as the stomach.

U.S. Pat. No. 4,159,021 to Casburn discloses a frame-like structure that protects an incision and is secured to a patent using adjustable straps. While this device may be readily mounted or removed from a patient, it is a highly customized device that is suitable only to protect a chest incision and receives vertical support from a strap mounted upon the patient's shoulder. Carrying such a frame may be burdensome for the patient and, furthermore, such an arrangement has little flexibility for application to other wounds.

U.S. Pat. No. 2,663,020 to Cushman discloses a pneumatic annular pad with a central opening positioned over the wound such that a bandage or clothing material may not come in contact with the wound. This pad may be sewn to a garment such that neither mounting straps nor adhesive to the patient's skin is necessary to support the pad. However, such a pneumatic pad is vulnerable to puncturing and becoming deflated and, furthermore, is limited in its application depending upon the size of the wound since the central opening must be capable of extending over a wound. In the instance of a chest incision which may extend 12–14 inches, such a pad may become cumbersome.

An object of the subject invention is to provide a wound protector that is convenient to apply and remove, with a minimum amount of inconvenience on behalf of the patient.

SUMMARY OF THE INVENTION

An apparatus used with clothing for maintaining a gap between clothing and a wound on the body of a patient is comprised of at least one spacer positioned on the inside of the clothing adjacent to the wound at a location which will space from the wound the clothing when it is worn by the patient. The apparatus further comprises a connector for securing the spacer to the clothing.

The spacer may be secured to the clothing in any of a variety of ways such as capturing the spacer against the clothing with a sleeve secured to the clothing. In the alternative, the spacer may be directly secured to the clothing using adhesive or stitches.

DETAILED DESCRIPTION OF THE EMBODIMENTS

Figure 1:
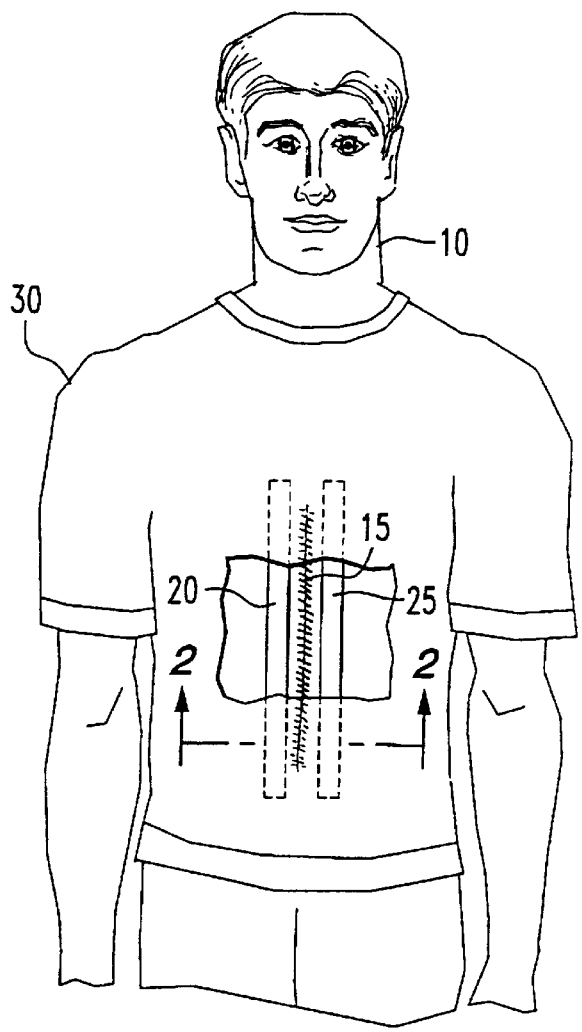
FIG. 1 is a front view of a patient showing one embodiment of the subject invention.

FIG. 1 illustrates a patient 10 with a wound 15 such as a chest incision that may be the result of a major surgical procedure. However, it should be noted that the wound 15 may be from any of a variety of causes and furthermore the shape of such a wound may not be linear, such as that illustrated in FIG. 1, but may have any of a variety of different shapes. Since such a wound is sensitive to even the slightest touching, the wound must be protected when the patient wears clothing or when bedding, such as a blanket, is placed over the patient.

Figure 2:
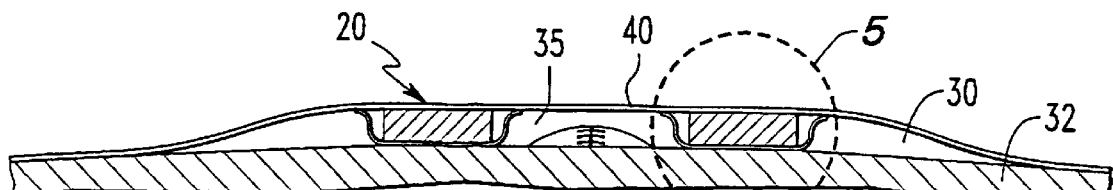
FIG. 2 is a section view taken along arrows 2—2 in FIG. 1.

FIGS. 1 and 2 illustrate two spacers 20 and 25, each positioned adjacent to the wound 15. Unlike previous designs, these spacers are not mounted to the patient's skin or held in place by straps around the patient but instead are mounted upon the clothing 30 worn by the patient. As illustrated in FIG. 1, the patient 10 wears clothing 30 such as an undershirt and the spacers 20 and 25 are connected to the inside of the undershirt 30. The spacers 20 and 25, either directly or indirectly as will be discussed, rest against the skin 32 to provide a gap 35 between the wound 15 and the material 40 of the clothing 30. The material of the clothing may be any material typically utilized in clothing; however, a material such as cotton or Lycra®, each of which is washable, may be preferred.

The spacers 20 and 25 may be connected to the material 40 of the clothing 30 in a variety of different ways.

Figure 3:
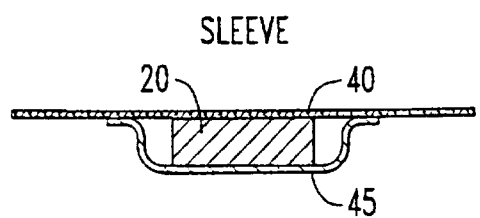
FIG. 3 illustrates the embodiment of the detail circled in FIG. 2 and labeled as 5.

FIG. 3 illustrates a cross section circled in FIG. 2 by item 5 showing a sleeve 45 secured to the material 40 of the clothing 30 to accommodate the spacer 20 which may be inserted within and extracted from the sleeve 45 at one of its ends. With this design the spacer 20 may be easily removed when the clothing is laundered. The sleeve 45 may be secured to the material 40 of the clothing 30 by stitching or in any number of ways known to those skilled in the art of fabricating clothing. The spacer 20 indirectly rests against the patient's skin 32 because it is separated from the patient's skin 32 by the sleeve 45.

Figure 4:
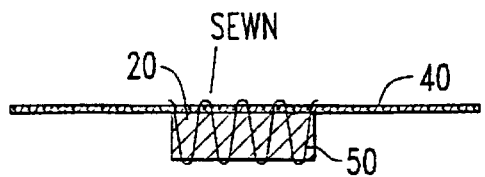
FIG. 4 illustrates another embodiment of the detail circled in FIG. 2 and labeled as 5.

FIG. 4 illustrates another embodiment of the portion circled as item 5 in FIG. 2 in which a sleeve is not used but the spacer 20 is sewn directly to the material 40 using stitching 50. Here the spacer 20 rests directly against the patient's skin 32.

Figure 5:
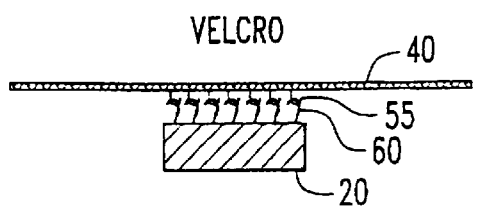
FIG. 5 illustrates another embodiment of the detail circled in FIG. 2 and labeled as 5.

In yet another embodiment, which is illustrated in FIG. 5, the spacer 20 is secured to the material 40 of the clothing utilizing interlocking hooked strips 55 and 60 such as Velcro® type adhesive strips attached to both the material 40 and the spacer 20. Just as with that embodiment discussed in FIG. 3, the spacer 20 may be removed when the clothing 30 is laundered.

Figure 6:
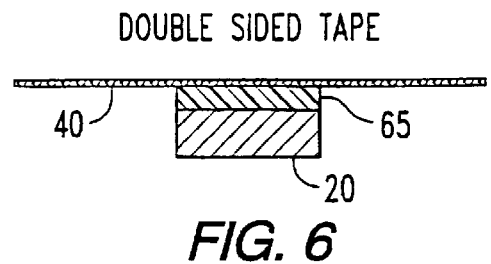
FIG. 6 illustrates another embodiment of the detail circled in FIG. 2 and labeled as 5.

FIG. 6 illustrates yet another embodiment by which the spacer 20 is secured to the material 40 utilizing a double-sided adhesive tape 65. Again, the strip 20 may be removed for laundering and a new strip of tape 65 may be applied to reconnect the spacer 20 to the material 40.

Figure 7:
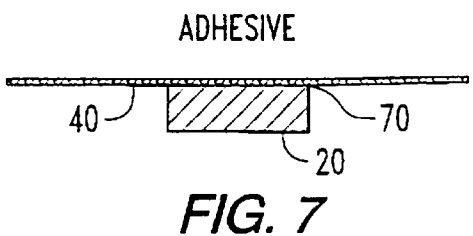
FIG. 7 illustrates another embodiment of the detail circled in FIG. 2 and labeled as 5.

FIG. 7 illustrates yet another embodiment in which the spacer 20 is secured to the material 40 utilizing the direct application of an adhesive 70 suitable for bonding the spacer material to the clothing material.

Figure 8:
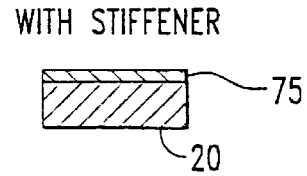
FIG. 8 is yet another embodiment illustrating the use of a stiffener with the spacer.

In the embodiment illustrated in FIG. 2, a sleeve 45 was utilized to retain the spacer 20 against the material 40. The spacer 20 is introduced to the sleeve 45 and pushed in at one end until it is positioned within the sleeve 45. In the event the sleeve 45 has a significant length, then it may be necessary to increase the stiffness of the spacer such that it does not buckle when being inserted into the sleeve 45. FIG. 8 illustrates a stiffener 75, such as a stiff strip of plastic, which may be directly attached to the spacer 20 to provide added stiffness to resist buckling when inserting the spacer 20 within the sleeve 45 illustrated in FIGS. 1 and 2.

The spacer may be made of any resilient, pliable material that is suitable to withstand moderate forces associated with those forces clothing may exert upon the skin while still maintaining the material at a distance sufficient from the wound to prevent contact of the material 40 against the wound 15. It should be noted that as the wound begins to heal, hair follicles begin to grow and in the early stages of growth these follicles are extremely sensitive such that the material 40 of the clothing 30 must also be separated from these hair follicles.

In the embodiments where the spacer 20 is located within the sleeve 45, the spacer 20 will not be directly contacting the patient's skin and therefore need not be selected on the basis of comfort against the skin. Therefore, the spacer may be made of, among other things, sponge, cloth or plastic.

In those embodiments in which a spacer 20 rests directly against the skin, it is necessary to provide a spacer material that will not irritate the skin. One such material is lamb's wool, although any number of a variety of materials that are not irritating to the skin may be appropriate.

To sufficiently space the material 40 from the skin, the thickness of the spacer should be between ⅛ and ⅝ inches. This thickness will be dependent upon the force the clothing material 40 exerts against the spacer 20. Additionally, the spacers must be thick enough such that if the clothing material 40 between the spacers 20, 25 becomes slack, the material is not able to drop a distance sufficient to contact the wound 15.

Figure 9:
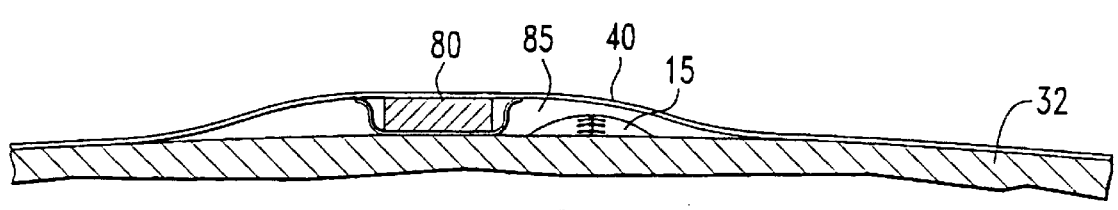
FIG. 9 is a section view similar to that of FIG. 2 utilizing only a single spacer.

While FIGS. 1 and 2 illustrate the use of two spacers 20 and 25, it is entirely possible to utilize a single spacer 80, as illustrated in FIG. 9. The spacer 80, which directly or indirectly through a sleeve rests upon the skin 32, must be positioned sufficiently close to the wound 15 and have a sufficient thickness so that the clothing material 40 is spaced from the wound 15 by a gap 85. This may require a spacer having a thickness greater than that thickness of the two spacers 20, 25 illustrated in FIGS. 1 and 2.

The single spacer illustrated in FIG. 9 may be secured to the material 40 of the clothing 30 in the same fashion as previously discussed for spacers 20 and 25.

While the wound 15 illustrated in FIG. 1 is essentially one-dimensional in that it is linear, it is entirely possible for the spacers of the subject invention to be utilized for wounds having more than one dimension.

Figure 10:
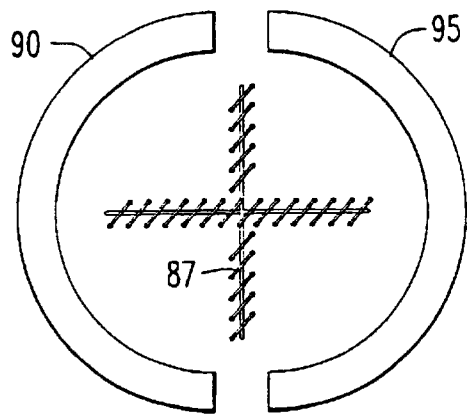
FIG. 10 is a schematic illustrating an arrangement of spacers that would be suitable to accommodate a wound extending over an area.

FIG. 10 illustrates a wound 87 which is two-dimensional and, as a result, spacers 90 and 95 may be positioned around the wound to provide a gap between the material (not shown) and the wound 87. Depending upon the contour of the wound 87, it may be entirely possible to utilize only a single spacer in a fashion similar to that previously discussed.

While the clothing 30 illustrated in FIG. 1 is an undershirt, the clothing may be an undershirt or any other garment such as a pair of pants or a dress shirt in the event the patient elects not to wear an undershirt.

Figure 11:
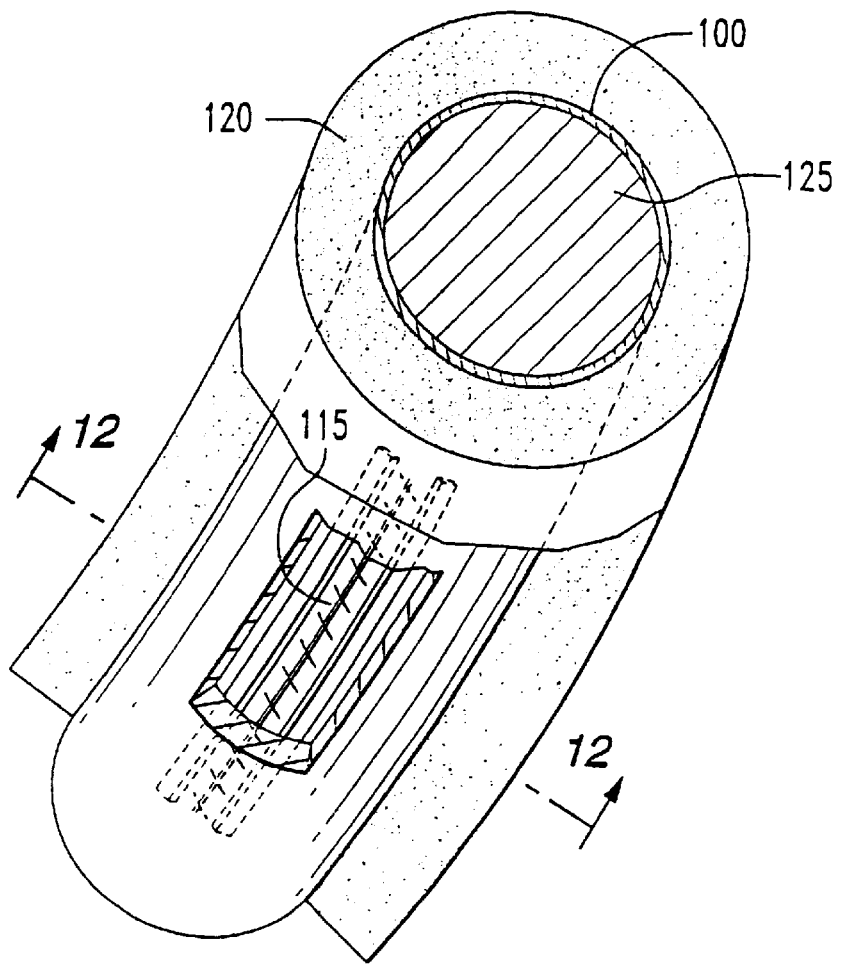
FIG. 11 illustrates the subject invention as applied to a sleeve which may be placed over a limb.
Figure 12:
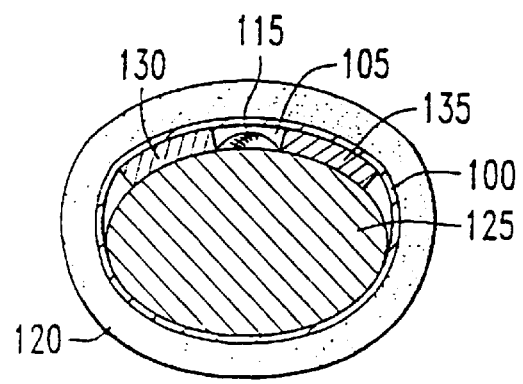
FIG. 12 is a section view along lines 12—12 illustrated in FIG. 11.

Furthermore, it is not necessary to limit the use of such spacers to clothing. In the event of a compound injury comprising, for example, a broken bone and a wound, it may be desirable, as illustrated in FIGS. 11 and 12, to utilize a cast 100 in conjunction with the spacers of the subject invention to provide a gap 105 for the wound 115. Under these circumstances, a cloth sleeve 120 may be placed over the limb 125 with spacers 130 and 135 connected to the inner material of the cloth sleeve 120 in a fashion similar to that previously identified for the material 40 of clothing 30. The cast 100 may then be placed around the sleeve 120 such that the gap 105 may be maintained not only between the cloth sleeve 120 and the wound 115 but furthermore between the cast 100 and the wound 115. Just as before, the spacers 130 and 135 must be thick enough and resilient enough to withstand the forces exerted by the cloth sleeve 120 and the cast 100 to maintain the gap 105 between the cloth sleeve 120 and the wound 115.

Just as previously discussed, it may be entirely possible to utilize a single spacer in lieu of two spacers 130, 135 to provide a gap 105 between the wound 115 and the cloth sleeve 120.

While the protection device has been described with respect to particular embodiments and configurations, numerous variations and modifications are possible using the described components of the device within the spirit and scope of the invention as described above and as defined and set forth in the appended claims.

I claim:

1. An apparatus used with clothing for maintaining a gap between an inside surface of the clothing and a wound on the body of a patient comprised of:

a) a piece of clothing;

b) at least one spacer positioned on the inside of the clothing adjacent to the wound at a location which will space the clothing from the wound when the clothing is worn by the patient and c) a connector attached to the inside surface of the clothing for securing the spacer to the clothing.

2. The apparatus according to claim 1 wherein the spacer is comprised of a resilient pliable material.

3. The apparatus according to claim 2 wherein the spacer is comprised of lamb's wool.

4. The apparatus according to claim 2 wherein the spacer is comprised of cloth.

5. The apparatus according to claim 2 wherein the spacer is comprised of sponge.

6. The apparatus according to claim 2 wherein the spacer is reinforced for stiffness.

7. The apparatus according to claim 2 wherein the spacer is comprised of a washable material.

8. The apparatus according to claim 2 wherein the spacer has a thickness of between ⅛ and ⅝ inches.

9. The apparatus according to claim 1 wherein two spacers are positioned upon the inside of the clothing adjacent the wound.

10. The apparatus according to claim 1 wherein one spacer is positioned upon the inside of the clothing adjacent the wound.

11. The apparatus according to claim 1 wherein the connector is a sleeve secured to the clothing to surround and capture the spacer at the location adjacent to the wound.

12. The apparatus according to claim 1 wherein the connector is sewn stitching attaching the spacer to the clothing.

13. The apparatus according to claim 1 wherein the connector is a pair of interlocking strips of hooks in which one strip is secured to the spacer and the other strip is secured to the clothing such that when the strips are mated, the spacer is secured to the clothing.

14. The apparatus according to claim 1 wherein the connector is adhesive between the spacer and the clothing.

15. The apparatus according to claim 1 wherein the connector is double sided tape between the spacer and the clothing.

16. The apparatus according to claim 1 wherein the clothing is a garment.

17. The apparatus according to claim 16 wherein the garment is a shirt.

18. The apparatus according to claim 16 wherein the garment is a pair of pants.

19. The apparatus according to claim 1 wherein the clothing is a protective sleeve used as the innermost layer of a cast.

20. An apparatus used with clothing for maintaining a gap between the clothing and a wound on the body of a patient comprised of:

a) at least one spacer made of a resilient pliable material and positioned on the inside of the clothing adjacent to the wound at a location which will space the clothing from the wound when the clothing is worn by the patient and b) a connector comprised of a sleeve attached to the clothing to surround and capture the spacer at the location adjacent to the wound.

* * * * *

UNITED STATES PATENT AND TRADEMARK OFFICE
CERTIFICATE OF CORRECTION

PATENT NO. : 6,041,786
DATED : March 28, 2000
INVENTOR(S) : Manuel DeLaTorre

It is certified that error appears in the above-identified patent and that said Letters Patent is hereby corrected as shown below:

Title Page, [56] References Cited, U.S. DOCUMENTS, reference 4 "3,026,824" should read --3,026,874--.

Signed and Sealed this

Sixth Day of March, 2001

Attest:

NICHOLAS P. GODICI

Attesting Officer

Acting Director of the United States Patent and Trademark Office